(12) United States Patent
Heller et al.

(10) Patent No.: US 7,731,707 B2
(45) Date of Patent: *Jun. 8, 2010

(54) ADJUSTABLE LENGTH CONVERSION ADAPTER FOR DILATATION CATHETERS

(75) Inventors: Gerald R. Heller, Bedford, MA (US); Wayne Mareiro, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1255 days.

This patent is subject to a terminal disclaimer.

(21) Appl. No.: 10/763,932

(22) Filed: Jan. 23, 2004

(65) Prior Publication Data

US 2004/0153050 A1 Aug. 5, 2004

Related U.S. Application Data

(63) Continuation of application No. 09/332,772, filed on Jun. 14, 1999, now Pat. No. 6,692,482.

(51) Int. Cl.
A61M 25/01 (2006.01)
(52) U.S. Cl. .................. 604/528; 604/103.04
(58) Field of Classification Search .............. 604/96.01, 604/164.01, 164.1, 264, 523, 528, 103.04; 606/192, 194
See application file for complete search history.

(56) References Cited

U.S. PATENT DOCUMENTS

| | | | |
|---|---|---|---|
| 4,710,181 A | 12/1987 | Fuqua | |
| 4,738,666 A | 4/1988 | Fuqua | |
| 4,763,653 A | 8/1988 | Rockey | |
| 4,798,586 A * | 1/1989 | Stevens | 604/96.01 |
| 5,021,044 A * | 6/1991 | Sharkawy | 604/510 |
| 5,183,464 A | 2/1993 | Dubrul et al. | |
| 5,267,982 A * | 12/1993 | Sylvanowicz | 604/532 |
| 5,382,238 A | 1/1995 | Abrahamson et al. | |
| 5,409,495 A | 4/1995 | Osborn | |

(Continued)

FOREIGN PATENT DOCUMENTS

EP 0 086 338 8/1983

Primary Examiner—Nicholas D Lucchesi
Assistant Examiner—Quynh-Nhu H Vu
(74) Attorney, Agent, or Firm—Crompton, Seager & Tufte, LLC (57) ABSTRACT

A device in the form of a conversion adapter for reducing an internal lumen of a catheter so as to accommodate a guidewire having a diameter substantially smaller than the internal lumen of the catheter as well as a catheter system including such a conversion adapter is provided. The adapter is positionable within the internal lumen of the catheter. The adapter has an external diameter which is substantially equal to the internal lumen of the catheter and further includes a smaller internal lumen which is substantially equal in diameter to the guidewire and is therefore capable of accommodating the smaller diameter guidewire therethrough. Preferably, the adapter extends within the internal lumen of the catheter along the entire length thereof, and preferably extends beyond the length of the catheter, including a flexible tapered tip at the end portion. In alternate embodiments, the adapter is slidably positionable and removable within the internal lumen of the catheter, thus providing a catheter system which is capable of effectively accommodating guidewires of two different diameters, without creating a drastic transition between the catheter tip and the guidewire and without compromising strength of the delivery system.

16 Claims, 3 Drawing Sheets

U.S. PATENT DOCUMENTS

| | | |
|---|---|---|
| 5,571,094 A | 11/1996 | Sirhan |
| 5,599,327 A | 2/1997 | Sugahara et al. |
| 5,658,262 A | 8/1997 | Castaneda et al. |
| 5,741,429 A * | 4/1998 | Donadio et al. ................ 216/8 |
| 5,743,874 A | 4/1998 | Fischell et al. |
| 5,836,306 A | 11/1998 | Duane et al. |
| 5,891,154 A * | 4/1999 | Loeffler ..................... 623/1.11 |
| 6,120,511 A * | 9/2000 | Chan ........................... 606/96 |
| 6,692,482 B2 * | 2/2004 | Heller et al. ................ 604/528 |

* cited by examiner

ADJUSTABLE LENGTH CONVERSION ADAPTER FOR DILATATION CATHETERS

CRSOSS-REFERENCE TO RELATED APPLICATIONS

This application is a continuation of and claims priority to U.S. application Ser. No. 09/332,772, filed Jun. 14, 1999, now U.S. Pat. No. 6,692,482 which is incorporated herein by reference.

FIELD OF THE INVENTION

The present invention relates to a conversion dilator for use with dilatation catheters. More particularly, the present invention relates to an adaptor for converting a dilatation catheter for use with a smaller size guidewire.

BACKGROUND OF THE INVENTION

Catheters are well known for use with the human body as part of diagnostic or treatment procedures. Such devices are typically introduced through body lumens such as blood vessels and are advanced to the sight designated for diagnosis or treatment, which sight may be a particular vessel or organ. For example, it is well known in percutaneous transluminal coronary angioplasty (PTCA) procedures to introduce a small diameter catheter into a stenosis portion of a blood vessel caused by arteriosclerosis or the like. The PTCA procedure typically includes inserting such a catheter equipped with a dilator such as a balloon at its tip into the stenosis portion of the blood vessel and inflating the dilator so as to dilate the stenosis portion of the blood vessel, thereby improving blood flow at the distal side thereof.

During such PTCA procedures, a guidewire is typically first introduced into the blood vessel and positioned within the blood vessel at the area of the stenosis portion. The catheter equipped with the dilator is then inserted over the guidewire and advanced through the blood vessel to the area of treatment, for carrying out the necessary procedure. After dilation of the stenosis portion of the blood vessel, often times a vascular stent is implanted into the blood vessel in order to maintain the blood vessel in an open position.

Catheters and guidewires are supplied in a variety of sizes and diameters. Specific applications and procedures typically involve use of specific size catheters and guidewires. For example, due to the tortuous path of blood vessels in cardiology procedures, cardiologists typically prefer smaller diameter guidewires such as a 0.018 inch diameter catheter, since they include features which are amenable to such uses, including flexibility. On the other hand, radiologists may prefer to use a larger diameter catheter, such as a 0.035 inch catheter, for cost and ease of use for a particular application.

It is common place for end users such as physicians carrying out catheterization procedures to become accustomed to using one particular size guidewire in such procedures. Such a physician would therefore be reluctant to incorporate catheter systems which require use of a different size guidewire. For example, while a physician typically may prefer to use a 0.018 inch guidewire due to specific characteristics including tip transition, column strength, pushability, trackability and tensile strength, catheters systems which are designed for use with a different size guidewire, such as a 0.035 inch guidewire, are becoming more common place, for example, in percutaneous catheterization procedures, and specifically for those procedures involving delivery and employment of peripheral stents.

Accordingly, it is desirable to provide for the use of a smaller diameter guidewire with a larger diameter dilatation catheter.

SUMMARY OF THE INVENTION

The present invention is directed to a device in the form of a conversion adapter for reducing an internal lumen of a catheter so as to accommodate a guidewire having a diameter substantially smaller than the internal lumen of the catheter. As indicated, oftentimes a specific catheter, such as a balloon catheter, includes a lumen of a specific size inner diameter, such as 0.035 inches. The guidewire initially introduced into the vessel, however, may be of a much smaller size diameter, such as a 0.018 inch guidewire. While it may be possible to advance the catheter over the smaller diameter guidewire, doing so can result in a variety of problems, such as a drastic transition between the catheter tip and the guidewire created due to the drastic change in diameter between the two. Additionally, strength of the delivery system may be compromised due to the difference in size between the guidewire and catheter, creating a channel for the guidewire to twist or bunch up.

Accordingly, the present invention provides a catheter system including a conversion adapter for converting the inner lumen of a catheter to accommodate a guidewire having a diameter which is substantially smaller than the internal lumen of the catheter. The adapter is positionable within the internal lumen of the catheter. The adapter has an external diameter which is substantially equal to the internal lumen of the catheter and further includes a smaller internal lumen which is substantially equal in diameter to the guidewire and is therefore capable of accommodating the smaller diameter guidewire therethrough. Preferably, the adapter extends within the internal lumen of the catheter along the entire length thereof, and preferably extends beyond the length of the catheter, including a flexible tapered tip at the end portion. In particularly preferred embodiments, the external diameter of the adapter is about 0.035 inches, and the internal lumen of the adapter includes an internal diameter of about 0.018 inches for accommodating a guidewire of about the same diameter.

The present invention further provides a catheter system for use with a first guidewire having an external diameter and a second guidewire having an external diameter smaller than the first guidewire. The catheter system includes a catheter having a lumen defining an internal diameter capable of accommodating the first guidewire. The system further includes an adapter selectively positionable within the lumen of the catheter, with the adapter having an external diameter substantially equal to the internal diameter of the lumen of the catheter and further including a lumen having an internal diameter capable of accommodating a second guidewire of a smaller diameter than the first guidewire.

The adapter is preferably removably slidable within the lumen of the catheter. As such, the adapter can be adjusted so as to extend beyond the length of the catheter, and can be selectively removed from the lumen of the catheter such that the catheter can then accommodate the first guidewire of a larger diameter.

In particularly preferred embodiments, the catheter includes an expandable balloon portion, which may be used in conjunction with a radially expandable stent positioned thereabout for transluminal implantation. Furthermore, a sheath may extend about the entire catheter assembly for covering the catheter system including the stent during delivery to an area of implantation within a vessel.

Further, the present invention provides a catheter system for reducing the internal diameter of a lumen of a catheter. The catheter system includes a catheter having a lumen, and an adapter slidably positioned within the lumen of the catheter. The adapter extends beyond the length of the catheter and includes an outer diameter substantially equal to the lumen of the catheter and an inner diameter defining a lumen which is smaller than the lumen of the catheter.

Still further, the present invention provides a catheter system including a kit of parts for use with a plurality of guidewires having different diameters. Such catheter system includes a catheter including a lumen defining an internal diameter, and a plurality of adapters selectively positionable within the lumen of the catheter. Each of the plurality of adapters includes an external diameter which is substantially equal to the internal diameter of the lumen of the catheter. Moreover, each of the plurality of adapters further includes a lumen defining mutually distinct internal diameters capable of uniquely accommodating one of the plurality of guidewires therethrough. As such, a catheter system capable of mutually exclusive use with a plurality of different diameter guidewires is provided.

DETAILED DESCRIPTION OF THE INVENTION

The present invention provides a catheter system including a conversion adapter for converting the inner lumen of a catheter to accommodate a guidewire having a diameter which is substantially smaller than the inner diameter of the catheter. The conversion adapter of the present invention includes a longitudinal tubular adapter which has an external diameter which is substantially equal to an inner diameter of the internal lumen of the catheter and is positionable therein, as will be discussed in more detail herein. For purposes of the present invention, substantially equal shall mean that the corresponding diameters of two members, such as the catheter and the adapter or the adapter and the guidewire, are close enough in size so as to provide a close-fitting engagement between one such member and another such member, thereby permitting effective positioning of the members with respect to one another.

Figure 1:
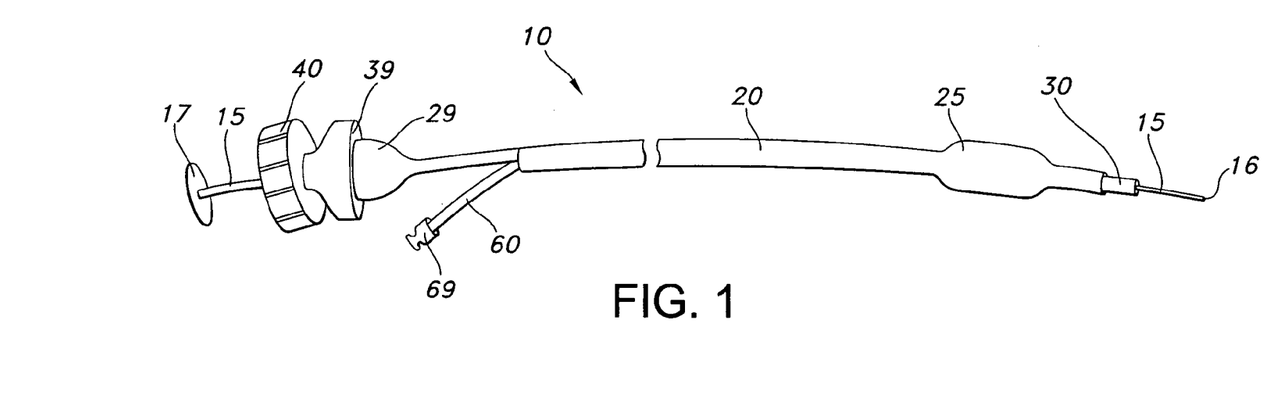
FIG. 1 depicts a perspective view of a catheter assembly according to the present invention.

Referring generally to the Figures, FIG. 1 depicts a catheter assembly 10 according to the present invention. Catheter assembly 10 includes a guidewire 15 extending therethrough. Guidewire 15 may be any guidewire as is known in the art. Guidewire is typically an elongated, relatively rigid cylindrical member. Guidewire 15 may be constructed of any material, but is preferably constructed of metal, such as stainless steel. Moreover, Guidewire 15 may be any known shape or form, preferably in the form of a helically would coil. Additionally, guidewire 15 may have a constant stiffness or flexibility along the entire length thereof, or may have portions of varying stiffness and flexibility, such as an area of increased flexibility at guidewire tip 16. Guidewire 15 may further include a coating along a portion or the entire length thereof, such as a lubricious or frictionless coating material. Guidewire 15 may further be provided with a radio opaque portion, for example in the form of a radio opaque coating on a portion of the guidewire, or by constructing a portion of the guidewire out of a radio opaque material.

Preferably, guidewire 15 includes a rounded tip 16 at the distal end thereof, and a control knob 17 at the proximal end thereof. Control knob 17 permits movement and guidance of guidewire 15 through a vessel during use.

Figure 2:
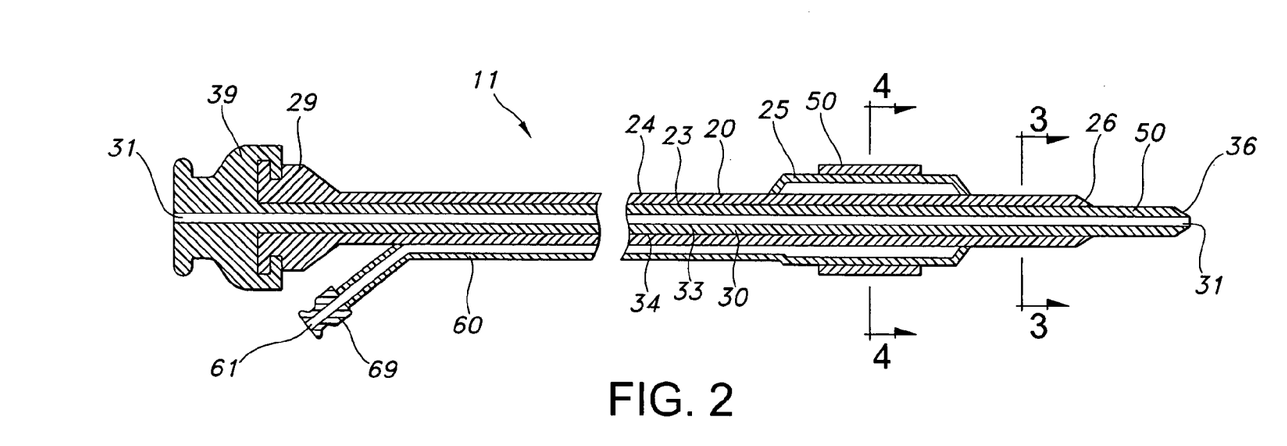
FIG. 2 depicts a longitudinal cross-sectional view of the catheter system according to the present invention.
Figure 3:
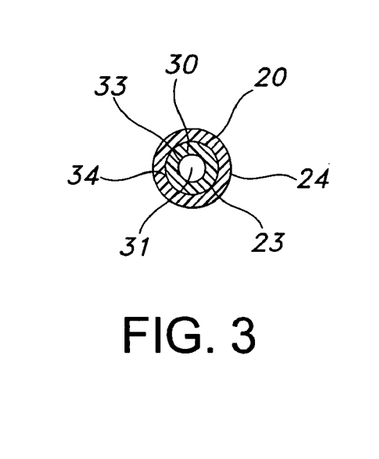
FIG. 3 depicts a cross-sectional view taken along lines 3-3' of FIG. 2.
Figure 4:
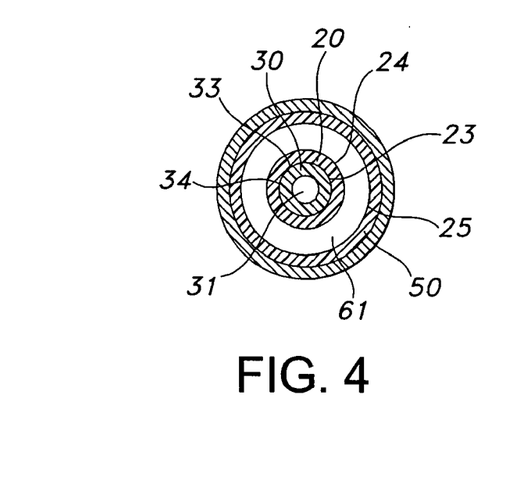
FIG. 4 depicts a cross-sectional view taken along lines 4-4' of FIG. 2.

Catheter assembly 10 further includes catheter system 11, as depicted in cross-sectional views in FIGS. 2, 3 and 4, for use in conjunction with guidewire 15. Catheter system 11 includes catheter 20 and conversion adapter 30.

Catheter 20 may be any type of catheter known in the art for use in conjunction with a guidewire, and is generally flexible along the length thereof. As shown in FIGS. 1 and 2, catheter 20 is a longitudinal tubular wall having an outer diameter 24 and an inner diameter 23 defined by an interior lumen 21. Catheter 20 may include a catheter tip 26 at the distal end thereof and a catheter hub 29 at the proximal end thereof. Catheter tip 26 is preferably tapered or conical in shape, providing a transition at the distal end of catheter 20.

Catheter 20 may be constructed of any biocompatible material known in the art. Preferably, catheter 20 is constructed of polymeric material, more preferably a polymeric material selected from polyethylene, polypropylene, polystyrene, polyester, polyurethane, polyamide, peboxes, and the like, and mixtures and combinations thereof.

Catheter 20 may further include a radially expandable portion, such as balloon 25. Such balloon catheters are well known in the art and are particularly useful in angioplasty procedures as well as delivery of intraluminal endoprostheses such as vascular stents and grafts. Balloon 25 may be constructed of any known material in the art. Preferably, balloon 25 is an elastomeric material capable of radial expansion, for example, polyurethane, polyethylene, polyamide, peboxes, and the like, and mixtures and combinations thereof. In embodiments incorporating such a balloon, an inflation port such as inflation port 60 including inflation lumen 61 may be provided, for example, extending within catheter assembly 10 in fluid communication with the interior of balloon 25. Inflation port 60 may further include inflation hub 69 at the proximal end thereof, for attachment to an inflation device for inflating balloon 25 in known manner.

Moreover, catheter 20 may support an endoprosthesis for intraluminal delivery by way of catheter 20 such as a stent, graft, stent/graft combination, or the like. Preferably, such endoprosthesis in the form of a stent 50, as shown positioned over balloon 25 in FIGS. 2 and 4. Such a stent is typically inserted into a damaged or diseased portion of a vessel in order to maintain the vessel in an open structure. Stent 50 may be any type of stent known in the art, and may be constructed of any known material. Preferably, stent 50 is a balloon expandable stent constructed of stainless steel, as is well known in the art.

As indicated, catheter 20 includes inner diameter 23 defining catheter lumen 21. Catheter system 11 further includes a conversion adapter 30 positionable within catheter lumen 21. Adapter 30 includes a longitudinal tubular wall which is generally flexible along the length thereof. Adapter 30 may further include an adapter tip 36 at the distal end thereof and an adapter hub 39 at the proximal end thereof. The adapter tip 36 is preferably tapered or conical in shape, providing a transition at the distal end of adapter 30 in a similar manner as catheter 20.

As shown in FIGS. 1 and 2, adapter 30 includes an outer diameter 34 and an inner diameter 33 defining an interior adapter lumen 31. Adapter lumen 31 is capable of accommodating a guidewire therethrough during use, as will be discussed in further detail herein.

Adapter 30 may be constructed of any biocompatible material, and may be a similar or different material than catheter 20. Preferably, adapter 30 is constructed of the same material as catheter 20, and is selected from a polymeric material, more preferably a polymeric material selected from polyethylene, polypropylene, polystyrene, polyester, polyurethane, polyamide, peboxes, and the like, and mixtures and combinations thereof.

Adapter 30 extends within catheter lumen 21 along the entire length of catheter 20. Preferably, adapter 30 extends beyond the length of catheter 20, as depicted in FIGS. 1 and 2. More preferably, the portion of adapter 30 which extends beyond catheter 20 includes a flexible tapered tip, providing flexibility and ease of insertion within a vessel. By providing a portion of adapter 30 extending beyond the length of catheter 20, a smooth transition is established between the external diameter of guidewire 15, adapter 30 and catheter 20. In this manner, a gradual transition can be selectively realized between the guidewire, the adapter and the external diameter of the catheter, providing for a smooth advancement through the blood vessel and reducing trauma to the vessel walls. Moreover, a longer, more flexible tip than would otherwise be present with catheter 20 may further be provided through such extending portion. Thus, in effect, the portion of adapter 30 extending beyond catheter 20 including adapter tip 36 acts as a dilator, thereby providing a dilatory effect during advancement of catheter system 11 through the blood vessel during use.

As best depicted in FIGS. 3 and 4, catheter 20 includes outer diameter 24 and inner diameter 23 defined by inner lumen 21. Further, adapter 30 includes outer diameter 34 and inner diameter 33 defined by inner lumen 31. Outer diameter 34 of adapter 30 and inner diameter 23 of catheter 20 are substantially equal in size. Thus, adapter 30 is positionable within inner lumen 21 of catheter 20 such that outer diameter 34 of adapter 30 and inner diameter 23 of catheter 20 create an engagement between adapter 30 and catheter 20.

Guidewires and catheters are well known in a variety of diameters and sizes. Accordingly, the outer diameters and inner diameters can be appropriately selected to fit the desired size. As indicated, outer diameter 34 of adapter 30 is substantially equal to inner diameter 23 of catheter 20, such that adapter 30 fits within catheter lumen 21 of catheter 20 in a close fitting manner to provide a smooth transition from catheter 20 to adapter 30, and if desired, permitting slidable movement of adapter 30 within catheter 20, as will be discussed in more detail herein. Moreover, inner diameter 33 of adapter 30 is substantially equal to the outer diameter of guidewire 15 to permit a similar close fitting, smooth transition from adapter 30 to guidewire 15. Desirably, guidewire 15 and inner diameter 33 of adapter 30 are substantially equal and are from about 0.014 to about 0.024 inches, most preferably about 0.018 inches. Additionally, outer diameter 34 of adapter 30 and inner diameter 23 of catheter 20 are substantially equal and are from about 0.035 to about 0.038 inches, most preferably about 0.035 inches.

Moreover, as depicted in FIG. 4, catheter 20 may further include balloon 25 extending about a portion of the external diameter 24 thereof. Stent 50 may further be provided extending about balloon 25.

Catheter 20 and adapter 30 may be fixed in position with respect to each other. For example, as depicted in FIGS. 1 and 2, catheter 20 may be attached to adapter 30 through catheter hub 29 and adapter hub 39. Such attachment may be a fixed attachment, but is desirably a releasable attachment, for example a threaded engagement between catheter hub 29 and adapter hub 39. Moreover, as depicted in FIG. 1, a connector 40 may be provided for further assisting in the connection of catheter 20 and adapter 30 and delivery of catheter assembly 10. Connector 40 may be any connector as known in the art. Preferably, connector 40 is a Touhy-Borst connector.

Figure 5:
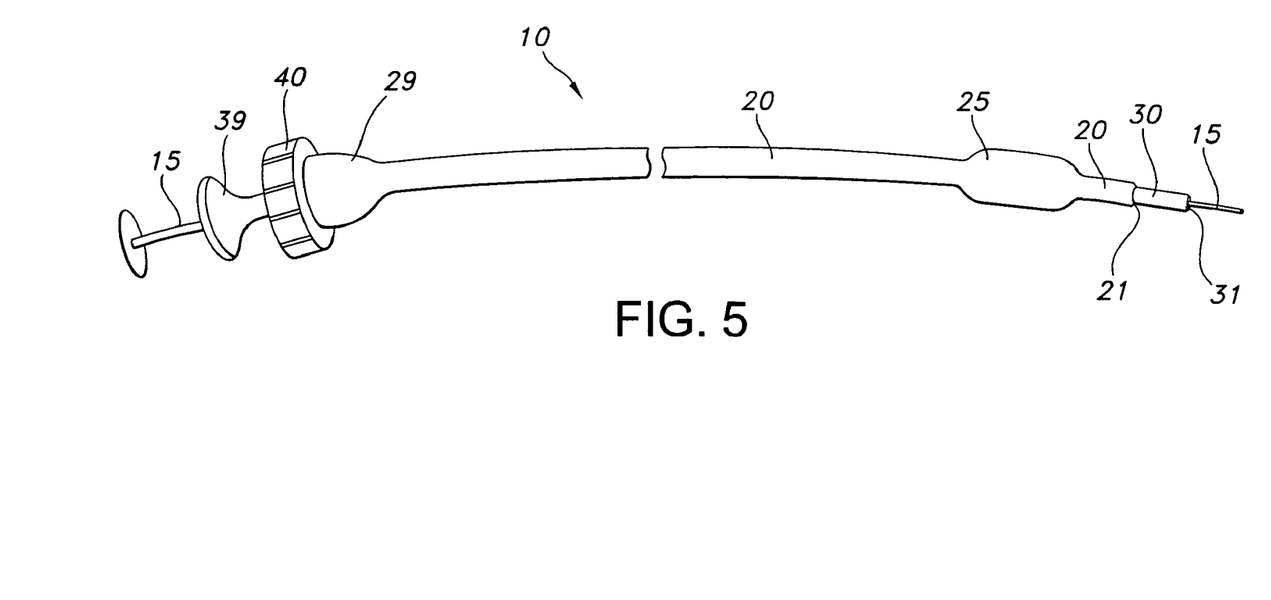
FIG. 5 depicts a perspective view of a catheter assembly according to an alternate embodiment of the present invention.

In an alternate embodiment of the present invention, adapter 30 may be selectively positionable within catheter lumen 21 of catheter 20. For example, as shown in FIG. 5, adapter hub 39 may be releasable from catheter hub 29 and/or connector 40, and the position of adapter 30 within lumen 21 of catheter 20 may be adjusted. This is preferably accomplished by providing a slidable engagement of adapter 30 within lumen 21 of catheter 20. As such, the distal portion of adapter 30 which extends beyond catheter tip 26 of catheter 20 can be selectively adjusted by an operator by slidably positioning adapter 30 to a desired position within lumen 21 of catheter 20. Preferably, adapter 30 is capable of maintaining a fixed position after being adjusted, for example by providing adapter hub 39 with a releasable connection to catheter hub 29 and/or connector 40. As such, the position of adapter 30 within catheter lumen 21 of catheter 20 can be repeatedly selectively adjusted, and can be maintained in any one of such selected positions by releasably connecting adapter hub 39.

More particularly, it may be desirable for catheter assembly 10 to include a larger flexible distal portion. In such an instance, adapter 30 can be slidably positioned within catheter lumen 21 of catheter 20 to provide an increased length of the distal portion of adapter 30 extending beyond the catheter tip 26 of catheter 20. Such additional length of adapter 30 provides for catheter assembly 10 having an increased smaller diameter at the distal end due to the smaller external diameter of adapter 30 as compared with the external diameter of catheter 20. As such, a more gradual transition from the guidewire diameter to the catheter diameter is accomplished, for example during positioning of the catheter assembly within a vessel.

In yet a further embodiment of the present invention, catheter system 11 is adaptable for use with different size guidewires. For example, catheter system 11 may be provided including catheter 20 and adapter 30 selectively positionable within catheter lumen 21, as described above. As such, catheter system 11 is capable of accommodating a guidewire of one diameter through adapter lumen 31 extending through adapter 30 in a fitting engagement, with the diameter of such guidewire being substantially equal to the inner diameter 33 of adapter 30. Additionally, with adapter 30 being removably selectively positionable within catheter lumen 21, adapter 30 can be removed from lumen 21 of catheter 20. Once removed, catheter 20 includes catheter lumen 21 extending therethrough which is of a greater internal diameter than adapter lumen 31 of adapter 30. Thus, catheter system 11 is further capable of accommodating a guidewire of a different diameter within catheter lumen 21. Accordingly, catheter system 11 can accommodate a guidewire having a diameter which is too small to be effectively positioned within catheter lumen 21 of catheter 20 by positioning adapter 30 within catheter lumen 21 such that the guidewire can be effectively accommodated in an appropriate fitting manner within adapter lumen 31 of adapter 30. On the other hand, catheter system 11 can also accommodate a guidewire having a diameter which is too large to fit within adapter lumen 31 of adapter 30 by removing adapter 31 from catheter lumen 21 of catheter 20, such that the larger diameter guidewire can be effectively accommodated in an appropriate fitting manner within catheter lumen 21 of catheter 20. Thus, a catheter system capable of use with at least two different diameter guidewires is provided.

Figure 6:
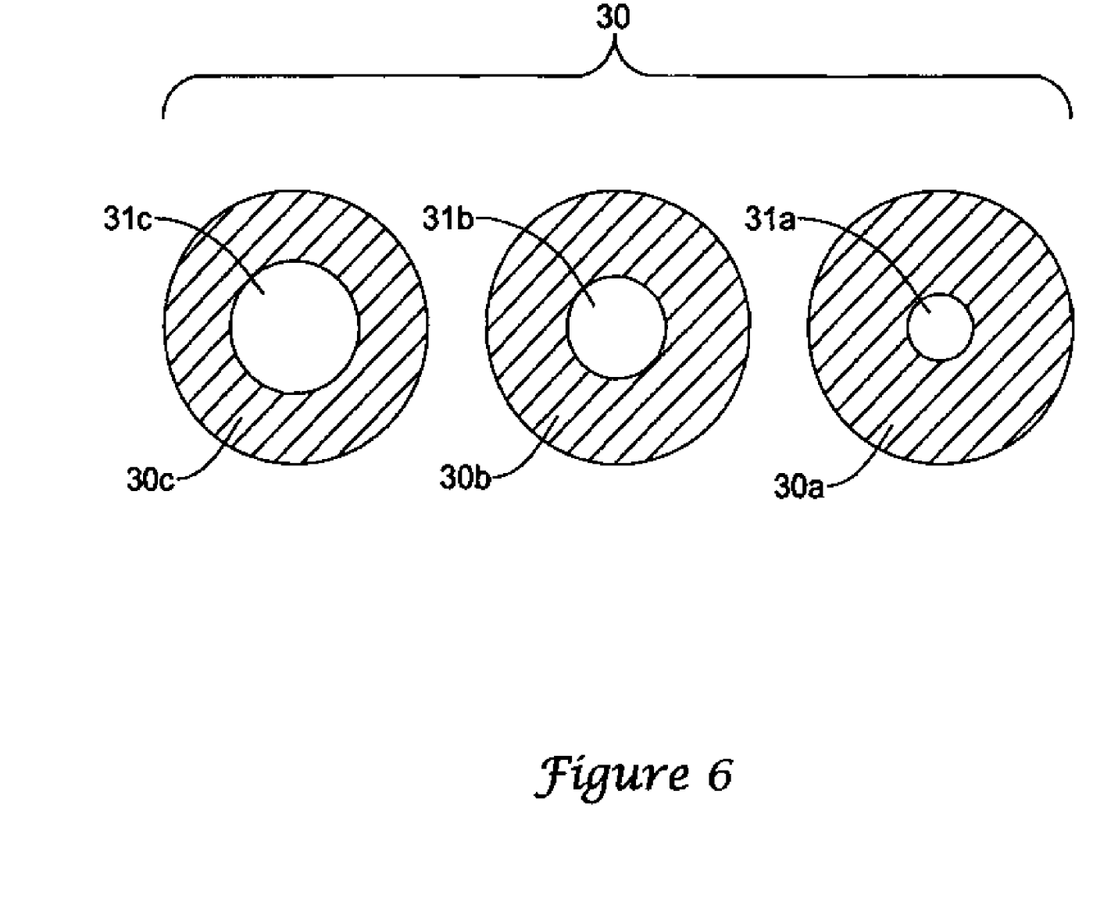
FIG. 6 depicts a plurality of adapters used in accordance with the catheter assembly of the present invention.

Moreover, the present invention contemplates a catheter system in the form of a kit of parts, which may include catheter 20 and a plurality of adapters 30, each individually selectively positionable within catheter lumen 21 of catheter 20. In such a catheter system, catheter 20 is provided as discussed above, including outer diameter 24 and inner diameter 23 defined by inner catheter lumen 21. Such a catheter system is further provided with a plurality of adapters 30, each being selectively positionable and insertable within catheter lumen 21 of catheter 20. Each of these plurality of adapters 30 includes an outer diameter 34 substantially equal to inner diameter 24 of catheter 20. Moreover, each of these plurality of adapters 30 includes an inner lumen 31 which defines a mutually distinct, different size inner diameter 33 for each respective adapter 30. For example, such a catheter system kit may include catheter 20 having inner lumen 21 with an inner diameter 23 of about 0.035 inches, and may further include three distinct adapters 30a, 30b, and 30c, as illustrated in FIG. 6, positionable within inner lumen 21 of catheter 20, each having an outer diameter of about 0.035 inches. Each of these three distinct adapters 30a, 30b, and 30c, however, further include an inner lumen 31a, 31b, and 31c, each inner lumen 31 defining a different inner diameter 33. For example, inner lumen 31a of the first adapter 30a may include an inner diameter of 0.018 inches for use in conjunction with a 0.018 inch diameter guidewire; inner lumen 31b of the second adapter 30b may include an inner diameter of 0.025 inches for use in conjunction with a 0.025 inch diameter guidewire; and inner lumen 31c of the third adapter 30c may include an inner diameter of 0.030 inches for use in conjunction with a 0.030 inch diameter guidewire. As such, any one of the plurality of adapters 30a, 30b, and 30c can be selectively positioned within catheter lumen 21 of catheter 20 as appropriate for the specific size guidewire desired for use. Accordingly, a catheter system capable of use with a plurality of different diameter guidewires is provided.

Having described the components of the present invention, use of the invention will now be described in terms of a preferred embodiment for implantation of a peripheral stent. In this preferred application, a needle (not shown) is inserted intraluminally into a vessel such as a blood vessel. Guidewire 15 is then inserted through the needle and advanced through the blood vessel to the area of implantation.

Catheter system 11 is then provided including catheter 20 and adapter 30 positioned therein, and further including balloon 25 with stent 50 positioned thereover. Catheter system 11 may further include a sheath extending externally thereabout in a tight manner, as is known in the art. Catheter system 11 is selected according to the diameter of guidewire 15. For example, if guidewire 15 is a larger diameter guidewire, such as a guidewire having a diameter of about 0.035 inches, adapter 30 may be selectively removed from catheter lumen 21 of catheter 20. As such, catheter lumen 21 can then accommodate the larger diameter guidewire therein such that guidewire 15 can be effectively positioned, and catheter 20 may be used in coordination with guidewire 15 for implantation in known manner. On the other hand, if guidewire 15 is a smaller diameter guidewire, for example a guidewire having an outer diameter of about 0.018 inches, catheter system 11 can be employed including adapter 30 within catheter lumen 21 of catheter 20. As such, adapter lumen 31 can accommodate guidewire 15 therein to provide an effective positioning of catheter system 11 about guidewire 15 such that guidewire 15 fits within adapter lumen 31 for effective delivery of catheter system 11 to the area of implantation.

With catheter system 11 positioned over guidewire 15, adapter tip 36 can be effectively adjusted with respect to catheter tip 26 to provide a desired transition for implantation. For example, connector 40 may be loosened to release adapter hub 39 and permit adapter 30 to be selectively slidable within catheter lumen 21 of catheter 20. Adapter 39 can then be slidably adjusted such that the adapter tip 36 at the distal end thereof extends beyond catheter tip 26 a selected distance, such as a distance of about 1 mm to about 10 mm. If desired, adapter hub 39 may then be reconnected to connector 40 in order to maintain adapter 30 in such selected position. In this manner, a gradual transition can be selectively realized between the guidewire, the adapter and the external diameter of the catheter, providing for a smooth advancement through the blood vessel and reducing trauma to the vessel walls. Thus, adapter tip 36 extending beyond catheter tip 26 effectively acts as a dilator, providing a dilatory effect during advancement of catheter system 11 through the blood vessel.

After reaching the area of implantation, the sheath is drawn distally away from catheter system 11, thereby exposing stent 50 to the interior surface of the blood vessel. Balloon 25 may then be inflated in known manner, causing radial expansion of stent 50. Such expansion causes stent 50 to contact the inner wall of the blood vessel. Stent 50 can then be anchored in place within the blood vessel in known manner, for instance by sutures, anchoring barbs and the like. After deployment of the stent, balloon 25 can be deflated, and catheter system 11 can be completely removed from the blood vessel.

While the present invention has been described in terms of a preferred embodiment and use, those skilled in the art will readily recognize that various modifications can be made without departing from the scope of the present invention.

What is claimed is:

1. A catheter system comprising:
    a first guidewire having a first external diameter and a second guidewire having a second external diameter smaller than said first external diameter;
    a catheter including a lumen defining an internal diameter substantially equal to said first external diameter of said first guidewire for fitting accommodation thereof;
    wherein said catheter includes an expandable balloon portion; and
    an adapter selectively positionable within said lumen of said catheter, said adapter including an external diameter substantially equal to said internal diameter of said lumen of said catheter, said adapter further including a lumen defining an internal diameter substantially equal to said second external diameter of said second guidewire for fining accommodation thereof.

2. A catheter system according to claim 1, wherein said adapter is removably slidable within said lumen of said catheter.

3. A catheter system according to claim 2, wherein said adapter extends beyond the length of said catheter, said portion extending beyond said catheter being adjustable by slidably positioning said adapter within said lumen of said catheter.

4. A catheter system according to claim 3, wherein said portion of said adapter extending beyond the length of said catheter includes a flexible tapered tip.

5. A catheter system according to claim 1, wherein said catheter includes a radially expandable stent for transluminal implantation.

6. A catheter system according to claim 5, wherein said radially expandable stent is a balloon expandable stent positioned about said expandable balloon portion.

7. A catheter system according to claim 1, wherein said lumen of said catheter is about 0.035 inches and said lumen of said adapter is about 0.018 inches.

8. A catheter system configured for use with a plurality of differently sized guidewires, the catheter system comprising:
a catheter having an inner diameter;
a guidewire extending through the catheter, the guidewire having an outer diameter;
a first adapter having an outer diameter substantially equal to the inner diameter of the catheter and a first inner diameter;
a second adapter having an outer diameter substantially equal to the inner diameter of the catheter and a second inner diameter;
wherein the first inner diameter is substantially equal to the outer diameter of the guidewire;
wherein the second inner diameter is different from the first inner diameter; and
wherein the first adapter is disposed between the catheter and the guidewire.

9. The catheter system of claim 8, wherein the catheter including a balloon.

10. The catheter system of claim 8, wherein the adapter is slidably disposed within the catheter.

11. The catheter system of claim 8, wherein the adapter including an adapter hub and the catheter includes a catheter hub releasably engaged with the adapter hub.

12. A method for configuring a catheter system, the method comprising:
providing a catheter having an inner diameter;
providing a guidewire having an outer diameter;
providing a plurality of adapters, wherein each of the plurality of adapters has an outer diameter substantially equal to the inner diameter of the catheter, and wherein each of the plurality of adapters has a different inner diameter;
selecting an adapter from the plurality of adapters that has an inner diameter substantially equal to the outer diameter of the guidewire;
disposing the adapter within the catheter; and
disposing the guidewire within the adapter.

13. The method of claim 12, wherein the catheter includes a balloon.

14. The method of claim 12, wherein the adapter is slidably disposed within the catheter.

15. The method of claim 12, wherein the adapter including an adapter hub and the catheter includes a catheter hub releasably engaged with the adapter hub.

16. The method of claim 12, further comprising:
removing the guidewire from the adapter;
removing the adapter from catheter;
providing a second guidewire having a second outer diameter different from the outer diameter of the guidewire;
selecting a second adapter from the plurality of adapters that has a second inner diameter substantially equal to the second outer diameter;
disposing the second adapter within the catheter; and
disposing the second guidewire within the second adapter.

* * * * *

UNITED STATES PATENT AND TRADEMARK OFFICE
CERTIFICATE OF CORRECTION

PATENT NO. : 7,731,707 B2  Page 1 of 1
APPLICATION NO. : 10/763932
DATED : June 8, 2010
INVENTOR(S) : Gerald R. Heller et al.

It is certified that error appears in the above-identified patent and that said Letters Patent is hereby corrected as shown below:

Column 8
Line 59: delete "fining", and insert therefor -- fitting --.

Signed and Sealed this

Thirty-first Day of August, 2010

David J. Kappos
*Director of the United States Patent and Trademark Office*